(12) United States Patent
Marnfeldt

(10) Patent No.: US 9,802,052 B2
(45) Date of Patent: Oct. 31, 2017

(54) METHOD AND APPARATUS FOR PROGRAMMING COMPLEX NEUROSTIMULATION PATTERNS

(71) Applicant: Boston Scientific Neuromodulation Corporation, Valencia, CA (US)

(72) Inventor: Goran N. Marnfeldt, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 64 days.

(21) Appl. No.: 14/926,725

(22) Filed: Oct. 29, 2015

(65) Prior Publication Data

US 2016/0121126 A1    May 5, 2016

Related U.S. Application Data

(60) Provisional application No. 62/075,079, filed on Nov. 4, 2014.

(51) Int. Cl.
*A61N 1/08* (2006.01)
*A61N 1/372* (2006.01)
(Continued)

(52) U.S. Cl.
CPC ....... *A61N 1/37247* (2013.01); *A61N 1/3605* (2013.01); *A61N 1/36167* (2013.01); *G06F 19/3406* (2013.01)

(58) Field of Classification Search
CPC .............. A61N 1/37247; A61N 1/3605; A61N 1/36167; G06F 19/3406
(Continued)

(56) References Cited

U.S. PATENT DOCUMENTS

| | | | |
|---|---|---|---|
| 4,255,790 A | 3/1981 | Hondeghem | |
| 4,931,858 A | 6/1990 | Honjo et al. | |

(Continued)

FOREIGN PATENT DOCUMENTS

| | | |
|---|---|---|
| WO | WO-03051175 A2 | 6/2003 |
| WO | WO-2006029257 A2 | 3/2006 |

(Continued)

OTHER PUBLICATIONS

U.S. Appl. No. 14/853,589, filed Sep. 14, 2015, Graphical User Interface for Programming Neurostimulation Pulse Patterns.
(Continued)

*Primary Examiner* — Michael Carey
(74) *Attorney, Agent, or Firm* — Schwegman Lundberg & Woessner, P.A.

(57) ABSTRACT

An example of a neurostimulation system may include a storage device, a programming control circuit, and a graphical user interface (GUI). The storage device may be configured to store a stimulation waveform representing a pattern of neurostimulation pulses. The programming control circuit may be configured to generate stimulation parameters controlling delivery of the neurostimulation pulses according to the stimulation waveform. The GUI may be configured to define the stimulation waveform as a function of one or more adjustable parameter curves each being a function of time. The one or more adjustable parameter curves each represent a user-programmable parameter. The GUI includes a waveform definition module that may be configured to present the stimulation waveform, present each parameter curve of the one or more adjustable parameter curves, allow for adjustment of the each parameter curve, and update the stimulation waveform in response to the adjustment of the each parameter curve.

20 Claims, 7 Drawing Sheets

(51) Int. Cl.
*A61N 1/36* (2006.01)
*G06F 19/00* (2011.01)

(58) Field of Classification Search
USPC .................................. 607/2, 59, 60, 66, 68
See application file for complete search history.

(56) References Cited

U.S. PATENT DOCUMENTS

| | | | |
|---|---|---|---|
| 4,935,674 A | 6/1990 | Rodriguez-cavazos | |
| 5,360,437 A | 11/1994 | Thompson | |
| 5,369,224 A | 11/1994 | Miyata | |
| 5,713,937 A | 2/1998 | Nappholz et al. | |
| 5,724,985 A | 3/1998 | Snell et al. | |
| 6,266,566 B1 | 7/2001 | Nichols et al. | |
| 6,516,227 B1 | 2/2003 | Meadows et al. | |
| 6,675,046 B2 | 1/2004 | Holsheimer | |
| 6,895,280 B2 | 5/2005 | Meadows et al. | |
| 6,993,384 B2 | 1/2006 | Bradley et al. | |
| 7,003,349 B1 | 2/2006 | Andersson et al. | |
| 7,317,948 B1 | 1/2008 | King et al. | |
| 7,333,856 B1 | 2/2008 | Er et al. | |
| 7,333,857 B2 | 2/2008 | Campbell | |
| 7,539,538 B2 | 5/2009 | Parramon et al. | |
| 7,650,184 B2 | 1/2010 | Walter | |
| 7,664,849 B1 * | 2/2010 | Chandler ............. | G06F 11/0727 709/224 |
| 7,783,353 B2 | 8/2010 | Libbus et al. | |
| 7,826,901 B2 | 11/2010 | Lee et al. | |
| 7,979,119 B2 | 7/2011 | Kothandaraman et al. | |
| 7,979,133 B2 | 7/2011 | Feler et al. | |
| 7,983,762 B2 | 7/2011 | Gliner et al. | |
| 8,019,439 B2 | 9/2011 | Kuzma et al. | |
| 8,224,453 B2 | 7/2012 | De Ridder | |
| 8,255,057 B2 | 8/2012 | Fang et al. | |
| 8,285,389 B2 | 10/2012 | Libbus et al. | |
| 8,355,797 B2 | 1/2013 | Caparso et al. | |
| 8,455,716 B2 | 6/2013 | Huang et al. | |
| 8,504,147 B2 | 8/2013 | Deem et al. | |
| 8,560,080 B2 | 10/2013 | Goetz | |
| 8,615,300 B2 | 12/2013 | Feler et al. | |
| 8,649,874 B2 | 2/2014 | Alataris et al. | |
| 8,670,831 B2 | 3/2014 | Wacnik et al. | |
| 8,676,329 B2 | 3/2014 | Wacnik et al. | |
| 8,676,331 B2 | 3/2014 | Parker | |
| 8,692,843 B2 | 4/2014 | Bloemer | |
| 8,694,113 B2 | 4/2014 | Smoorenburg | |
| 8,731,675 B2 | 5/2014 | Ranu et al. | |
| 8,751,009 B2 | 6/2014 | Wacnik | |
| 8,798,755 B2 | 8/2014 | Grill et al. | |
| 8,874,211 B2 | 10/2014 | Libbus et al. | |
| 9,265,948 B2 | 2/2016 | Libbus et al. | |
| 2002/0077669 A1 | 6/2002 | Lindh et al. | |
| 2002/0077859 A1 | 6/2002 | Stahmann et al. | |
| 2002/0115939 A1 | 8/2002 | Mulligan et al. | |
| 2003/0139781 A1 | 7/2003 | Bradley et al. | |
| 2003/0176899 A1 | 9/2003 | Samuelsson et al. | |
| 2004/0111131 A1 | 6/2004 | Hu et al. | |
| 2005/0177206 A1 | 8/2005 | North et al. | |
| 2006/0149337 A1 | 7/2006 | John | |
| 2006/0241720 A1 | 10/2006 | Woods et al. | |
| 2007/0150036 A1 | 6/2007 | Anderson | |
| 2007/0299663 A1 | 12/2007 | Fado et al. | |
| 2008/0158175 A1 | 7/2008 | Hotelling et al. | |
| 2008/0163097 A1 | 7/2008 | Goetz et al. | |
| 2008/0188909 A1 | 8/2008 | Bradley | |
| 2009/0024189 A1 | 1/2009 | Lee et al. | |
| 2009/0043359 A1 | 2/2009 | Smoorenburg | |
| 2009/0198305 A1 | 8/2009 | Naroditsky et al. | |
| 2009/0204173 A1 | 8/2009 | Fang et al. | |
| 2010/0010390 A1 | 1/2010 | Skelton et al. | |
| 2010/0010566 A1 | 1/2010 | Thacker et al. | |
| 2010/0010646 A1 | 1/2010 | Drew et al. | |
| 2010/0121409 A1 | 5/2010 | Kothandaraman et al. | |
| 2010/0274312 A1 | 10/2010 | Alataris et al. | |
| 2010/0274314 A1 | 10/2010 | Alataris et al. | |
| 2010/0274315 A1 | 10/2010 | Alataris et al. | |
| 2010/0274317 A1 | 10/2010 | Parker et al. | |
| 2010/0274318 A1 | 10/2010 | Walker et al. | |
| 2010/0274326 A1 | 10/2010 | Chitre et al. | |
| 2011/0046697 A1 | 2/2011 | Gerber et al. | |
| 2011/0054570 A1 | 3/2011 | Lane | |
| 2011/0093051 A1 | 4/2011 | Davis et al. | |
| 2011/0208012 A1 | 8/2011 | Gerber et al. | |
| 2012/0059446 A1 | 3/2012 | Wallace et al. | |
| 2012/0083709 A1 | 4/2012 | Parker et al. | |
| 2012/0109006 A1 | 5/2012 | James et al. | |
| 2012/0197336 A1 | 8/2012 | Su | |
| 2012/0253422 A1 | 10/2012 | Thacker et al. | |
| 2012/0265267 A1 | 10/2012 | Blum et al. | |
| 2012/0265279 A1 | 10/2012 | Zhu et al. | |
| 2012/0283797 A1 | 11/2012 | De Ridder | |
| 2012/0290041 A1 | 11/2012 | Kim et al. | |
| 2012/0296396 A1 | 11/2012 | Moffitt et al. | |
| 2013/0041283 A1 | 2/2013 | Wichner | |
| 2013/0053926 A1 | 2/2013 | Hincapie Ordonez et al. | |
| 2013/0060304 A1 | 3/2013 | Wichner | |
| 2013/0066411 A1 | 3/2013 | Thacker et al. | |
| 2013/0116752 A1 | 5/2013 | Parker et al. | |
| 2013/0131760 A1 | 5/2013 | Rao et al. | |
| 2013/0226261 A1 | 8/2013 | Sparks et al. | |
| 2013/0268021 A1 | 10/2013 | Moffitt | |
| 2013/0296975 A1 | 11/2013 | Lee et al. | |
| 2013/0304152 A1 | 11/2013 | Bradley et al. | |
| 2014/0005743 A1 | 1/2014 | Giuffrida et al. | |
| 2014/0052033 A1 | 2/2014 | Lawlis et al. | |
| 2014/0067016 A1 | 3/2014 | Kaula et al. | |
| 2014/0074179 A1 | 3/2014 | Heldman et al. | |
| 2014/0074180 A1 | 3/2014 | Heldman et al. | |
| 2014/0074190 A1 | 3/2014 | Griffith | |
| 2014/0081349 A1 | 3/2014 | Lee et al. | |
| 2014/0081354 A1 | 3/2014 | Davis et al. | |
| 2014/0172045 A1 | 6/2014 | Yip et al. | |
| 2014/0257425 A1 | 9/2014 | Arcot-Krishnamurthy et al. | |
| 2014/0257428 A1 * | 9/2014 | Zhu ................... | A61N 1/36178 607/46 |
| 2014/0276181 A1 | 9/2014 | Sun et al. | |
| 2014/0277267 A1 | 9/2014 | Vansickle et al. | |
| 2015/0012057 A1 | 1/2015 | Carlson et al. | |
| 2015/0051666 A1 | 2/2015 | Roy et al. | |
| 2015/0165209 A1 | 6/2015 | Grandhe et al. | |
| 2015/0224307 A1 | 8/2015 | Bolea | |
| 2015/0238762 A1 | 8/2015 | Pal et al. | |
| 2015/0297893 A1 | 10/2015 | Kokones et al. | |
| 2015/0328461 A1 | 11/2015 | Charlesworth et al. | |
| 2015/0328462 A1 | 11/2015 | Griffith | |
| 2015/0328467 A1 | 11/2015 | Demers et al. | |
| 2015/0343242 A1 | 12/2015 | Tyler et al. | |
| 2016/0027293 A1 | 1/2016 | Esteller et al. | |
| 2016/0074662 A1 | 3/2016 | Moffitt et al. | |
| 2016/0074663 A1 | 3/2016 | De Ridder | |
| 2016/0279429 A1 | 9/2016 | Hershey et al. | |
| 2017/0050033 A1 | 2/2017 | Wechter | |
| 2017/0106197 A1 | 4/2017 | Wechter et al. | |

FOREIGN PATENT DOCUMENTS

| | | |
|---|---|---|
| WO | WO-2006135791 A2 | 12/2006 |
| WO | WO-2009067610 A1 | 5/2009 |
| WO | WO-2016004230 A1 | 1/2016 |
| WO | WO-2016044169 A1 | 3/2016 |
| WO | WO-2016073271 A1 | 5/2016 |
| WO | WO-2016154375 A1 | 9/2016 |
| WO | WO-2016172239 A1 | 10/2016 |
| WO | WO-2017019191 A1 | 2/2017 |
| WO | WO-2017066187 A1 | 4/2017 |

OTHER PUBLICATIONS

"U.S. Appl. No. 14/853,589, Final Office Action dated Jan. 18, 2017", 12 pgs.

"U.S. Appl. No. 14/853,589, Non Final Office Action dated Aug. 17, 2016", 14 pgs.

(56) References Cited

OTHER PUBLICATIONS

"U.S. Appl. No. 14/853,589, Notice of Allowance dated Apr. 17, 2017", 5 pgs.
"U.S. Appl. No. 14/853,589, Response filed Mar. 14, 2017 to Final Office Action dated Jan. 18, 2017", 12 pgs.
"U.S. Appl. No. 14/853,589, Response filed Nov. 17, 2016 to Non Final Office Action dated Aug. 17, 2016", 12 pgs.
"International Application Serial No. PCT/US15/58017, International Search Report dated Apr. 6, 2016", 5 pgs.
"International Application Serial No. PCT/US15/58017, Written Opinion dated Apr. 6, 2016", 8 pgs.
"International Application Serial No. PCT/US2015/049993, International Preliminary Report on Patentability dated Mar. 30, 2017", 6 pgs.
"International Application Serial No. PCT/US2015/049993, International Search Report dated Jan. 14, 2016", 3 pgs.
"International Application Serial No. PCT/US2015/049993, Written Opinion dated Jan. 14, 2016", 4 pgs.
"International Application Serial No. PCT/US2015/058017, International Preliminary Report on Patentability dated May 18, 2017", 10 pgs.
"International Application Serial No. PCT/US2016/023888, International Search Report dated Jun. 6, 2016", 5 pgs.
"International Application Serial No. PCT/US2016/023888, Written Opinion dated Jun. 6, 2016", 5 pgs.
"International Application Serial No. PCT/US2016/037226, International Search Report dated Aug. 25, 2016", 4 pgs.
"International Application Serial No. PCT/US2016/037226, Written Opinion dated Aug. 25, 2016", 5 pgs.
"International Application Serial No. PCT/US2016/056426, International Search Report dated Jan. 26, 2017", 5 pgs.
"International Application Serial No. PCT/US2016/056426, Written Opinion dated Jan. 26, 2017", 6 pgs.
Moffitt, Michael A., et al., "Graphical User Interface for Programming Neurostimulation Pulse Patterns", U.S. Appl. No. 14/853,589, filed Sep. 14, 2015.
Rao, Prakash, et al., "Technique for Linking Electrodes Together During Programming of Neurostimulation System", U.S. Appl. No. 61/561,760, filed Nov. 18, 2011.
Vansickle, Dennis Allen, "Systems and Methods for Delivering Sub-Threshold Therapy to a Patient", U.S. Appl. No. 61/801,917, filed Mar. 15, 2013.

\* cited by examiner

METHOD AND APPARATUS FOR PROGRAMMING COMPLEX NEUROSTIMULATION PATTERNS

CLAIM OF PRIORITY

This application claims the benefit of priority under 35 U.S.C. §119(e) of U.S. Provisional Patent Application Ser. No. 62/075,079, filed on Nov. 4, 2014, which is herein incorporated by reference in its entirety.

TECHNICAL FIELD

This document relates generally to neurostimulation and more particularly to a method and system for programming a stimulation waveform representing a pattern of neurostimulation pulses using a graphical user interface (GUI).

BACKGROUND

Neurostimulation, also referred to as neuromodulation, has been proposed as a therapy for a number of conditions. Examples of neurostimulation include Spinal Cord Stimulation (SCS), Deep Brain Stimulation (DBS), Peripheral Nerve Stimulation (PNS), and Functional Electrical Stimulation (FES). Implantable neurostimulation systems have been applied to deliver such a therapy. An implantable neurostimulation system may include an implantable neurostimulator, also referred to as an implantable pulse generator (IPG), and one or more implantable leads each including one or more electrodes. The implantable neurostimulator delivers neurostimulation energy through one or more electrodes placed on or near a target site in the nervous system. An external programming device is used to program the implantable neurostimulator with stimulation parameters controlling the delivery of the neurostimulation energy.

In one example, the neurostimulation energy is delivered in the form of electrical neurostimulation pulses. The delivery is controlled using stimulation parameters that specify spatial (where to stimulate), temporal (when to stimulate), and informational (patterns of pulses directing the nervous system to respond as desired) aspects of a pattern of neurostimulation pulses. M any current neurostimulation systems are programmed to deliver periodic pulses with one or a few uniform waveforms continuously or in bursts. However, the human nervous systems use neural signals having much more sophisticated patterns to communicate various types of information, including sensations of pain, pressure, temperature, etc. The nervous system may interpret an artificial stimulation with a simple pattern of stimuli as an unnatural phenomenon, and respond with an unintended and undesirable sensation and/or movement. For example, some neurostimulation therapies are known to cause paresthesia and/or vibration of non-targeted tissue or organ.

Recent research has shown that the efficacy and efficiency of certain neurostimulation therapies can be improved, and their side-effects can be reduced, by using patterns of neurostimulation pulses that emulate natural patterns of neural signals observed in the human body. While modern electronics can accommodate the need for generating such sophisticated pulse patterns, the cap ability of a neurostimulation system depends on its post-manufacturing programmability to a great extent. For example, a sophisticated pulse pattern may only benefit a patient when it is customized for that patient, and waveform patterns predetermined at the time of manufacturing may substantially limit the potential for the customization. In various applications, the customization may require pulse-by-pulse programmability, thereby making the programming of the complete pulse pattern a challenging task.

SUMMARY

An example (e.g., "Example 1") of a neurostimulation system may include a storage device, a programming control circuit, and a graphical user interface (GUI). The storage device may store a stimulation waveform representing a pattern of neurostimulation pulses during a stimulation period. The programming control circuit may be configured to generate a plurality of stimulation parameters controlling delivery of the neurostimulation pulses according to the stimulation waveform. The GUI is coupled to the storage device and the control circuit and may be configured to define the stimulation waveform as a function of one or more adjustable parameter curves each being a function of time during the stimulation period. The one or more adjustable parameter curves each represent a user-programmable parameter. The GUI includes a waveform definition module that may be configured to present the stimulation waveform, present each parameter curve of the one or more adjustable parameter curves, allow for adjustment of the each parameter curve, and update the stimulation waveform in response to the adjustment of the each parameter curve.

In Example 2, the subject matter of Example 1 may optionally be configured to further include a stimulation device and a programming device. The stimulation device includes a stimulation output circuit configured to deliver the neurostimulation pulses and a stimulation control circuit configured to control the delivery of the neurostimulation pulses using the plurality of stimulation parameters. The programming device communicatively coupled to the stimulation device and including the storage device, the programming circuit, and the GUI.

In Example 3, the subject matter of Example 2 may optionally be configured such that the stimulation device includes an implantable stimulator including an implant telemetry circuit configured to receive the plurality of stimulation parameters, and the programming device includes an external programmer including an external telemetry circuit configured to transmit the plurality of stimulation parameters to the implantable stimulator via a wireless telemetry link.

In Example 4, the subject matter of any one or any combination of Examples 1-3 may optionally be configured such that the waveform definition module is further configured to present one or more handles each placed on a parameter curve of the one or more adjustable parameter curves and allow for adjustment of the parameter curve by moving a handle of the one or more handles. The one or more handles each correspond to a value of the user-programmable parameter represented by the parameter curve.

In Example 5, the subject matter of Example 4 may optionally be configured such that the waveform definition module is further configured to allow for addition of a new handle to the one or more handles placed on the parameter curve and deletion of a handle from the one or more handles placed on the parameter curve.

In Example 6, the subject matter of any one or any combination of Examples 1-5 may optionally be configured such that the storage device may further store a pattern library including one or more template waveforms, and the waveform definition module is further configured to select a template waveform from the template library and present the selected template waveform as the stimulation waveform.

In Example 7, the subject matter of Example 6 may optionally be configured such that the waveform definition module is further configured to allow for adding the updated stimulation waveform as a new template waveform to the one or more template waveforms.

In Example 8, the subject matter of any one or any combination of Examples 1-7 may optionally be configured such that the waveform definition module is configured to present the stimulation waveform as an envelope curve with pulse type indicators. The envelope curve specifies on-periods each including one or more pulses of the neurostimulation pulses and off-periods including none of the neurostimulation pulses. The on-periods are each assigned to a pulse type of the one of more pulse types. The pulse type indicators each specify the pulse type to which one of the on-periods is assigned to.

In Example 9, the subject matter of Example 8 may optionally be configured such that the storage device may further store a pulse library including one or more pulse types, and the waveform definition module is further configured to allow for selection of one or more on-periods of the on-periods in the envelope curve and assignment of the selected one or more on-periods to the specified pulse type.

In Example 10, the subject matter of Example 9 may optionally be configured such that the waveform definition module is further configured to allow for creation of a new pulse type to be added to the pulse library and adjustment of each pulse type of the one or more pulse types in the pulse library.

In Example 11, the subject matter of Example 10 may optionally be configured such that the waveform definition module is further configured to present a pulse waveform of a pulse type selected from the one or more pulse types and allow for modification of the pulse waveform of the selected pulse type.

In Example 12, the subject matter of Example 11 may optionally be configured such that the waveform definition module is further configured to present one or more handles each placed on the pulse waveform of the selected pulse type, allow for selection of a handle from the one or more handles placed on the pulse waveform of the selected pulse type, and allow for the modification of the pulse waveform of the selected pulse type by moving the selected handle.

In Example 13, the subject matter of any one or any combination of Examples 1-12 may optionally be configured such that the waveform definition module configured to present a frequency curve of the one or more adjustable parameter curves, the frequency curve representing a pulse frequency, allow for adjustment of the frequency curve, and update the stimulation waveform in response to the adjustment of the frequency curve.

In Example 14, the subject matter of any one or any combination of Examples 1-13 may optionally be configured such that the waveform definition module configured to present a duration curve of the one or more adjustable parameter curves, the duration curve representing a pulse width, allow for adjustment of the duration curve, and update the stimulation waveform in response to the adjustment of the duration curve.

In Example 15, the subject matter of any one or any combination of Examples 1-14 may optionally be configured such that the waveform definition module configured to present an amplitude curve of the one or more adjustable parameter curves, the amplitude curve representing a pulse amplitude, allow for adjustment of the amplitude curve, and update the stimulation waveform in response to the adjustment of the amplitude curve.

An example (e.g., "Example 16") of a method for defining a neurostimulation by a user may include presenting a stimulation waveform on a graphical user interface (GUI). The stimulation waveform represents a pattern of neurostimulation pulses during a stimulation period and is a function of one or more adjustable parameter curves each being a function of time during the stimulation period, the one or more adjustable parameter curves each representing a user-programmable parameter. The method may further include presenting the one or more adjustable parameter curves on the GUI, allowing the user to adjust each parameter curve of the one or more adjustable parameter curves using the GUI, and updating the stimulation waveform in response to the adjustment of the each parameter curve.

In Example 17, the subject matter of Example 16 may optionally further include generating a plurality of stimulation parameters based on the stimulation waveform. The plurality of stimulation parameters allows for delivery of the neurostimulation from a stimulation device to be controlled according to the stimulation waveform.

In Example 18, the subject matter of presenting the stimulation waveform as found on Example 16 may optionally include presenting a template waveform, and the subject matter of Example 16 may optionally further include creating one or more template waveforms, storing the one or more template waveforms, and selecting the template waveform from the stored one or more waveforms.

In Example 19, the subject matter of creating the one or more template waveforms as found on Example 19 may optionally include creating one or more therapy-specific template waveforms for one or more types of neuro stimulation therapy.

In Example 20, the subject matter of any one or any combination of Examples 16-19 may optionally further include presenting one or more handles on the GUI, the one or more handles each placed on a parameter curve of the one or more adjustable parameter curves, allowing the user to select a handle of the one or more handles placed on the parameter curve, and allowing the user to adjust the parameter curve by moving the selected handle. The one or more handles each correspond to a value of the user-programmable parameter represented by the parameter curve.

In Example 21, the subject matter of Example 20 may optionally further include allowing the user to add a new handle to the one or more handles placed on the parameter curve and allowing the user to delete a handle of the one or more handles p laced on the parameter curve.

In Example 22, the subject matter of presenting the one or more adjustable parameter curves as found in any one or any combination of Examples 16-21 may optionally include presenting one or more of a frequency curve representing a pulse frequency, a duration curve representing a pulse width, and an amplitude curve representing a pulse amplitude.

In Example 23, the subject matter of presenting the stimulation waveform as found in any one or any combination of Examples 16-22 may optionally include presenting an envelope curve with pulse type indicators. The envelope curve specifies on-periods each including one or more pulses of the neurostimulation pulses and off-periods including none of the neurostimulation pulses. The on-periods are each assigned to a pulse type of the one of more pulse types. The pulse type indicators each specify the pulse type to which one of the on-periods is assigned to.

In Example 24, the subject matter of Example 23 may optionally further include storing the one or more pulse types, allowing the user to select one or more on-periods of the on-periods in the envelope curve, allowing the user to select a pulse type from the stored one or more pulse types, and allowing the user to assign the selected one or more on-periods to the selected pulse type.

In Example 25, the subject matter of Example 24 may optionally further include allowing the user to create a new pulse type using the GUI to add to the stored one or more pulse types, and allowing the user to modify each pulse type of the one or more pulse types using the GUI.

In Example 26, the subject matter of allowing the user to modify the each pulse type as found in Example 25 may optionally include presenting a pulse waveform of the each pulse type on the GUI, presenting one or more handles each placed on the pulse waveform of the each pulse type, allowing the user to select a handle from the one or more handles placed on the pulse waveform, and allowing the user to modify the pulse waveform by moving the selected handle.

In Example 27, the subject matter of any one or any combination of Examples 16-26 may optionally include transmitting the plurality of stimulation parameters to an implantable stimulator and controlling delivery of the neurostimulation pulses from the implantable stimulator using the plurality of stimulation parameters.

This Summary is an overview of some of the teachings of the present application and not intended to be an exclusive or exhaustive treatment of the present subject matter. Further details about the present subject matter are found in the detailed description and app ended claims. Other aspects of the disclosure will be apparent to persons skilled in the art up on reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
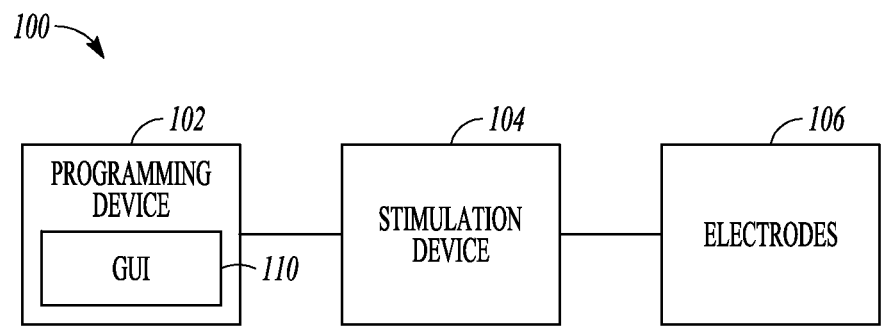
FIG. 1 illustrates an embodiment of a neurostimulation system.

In the following detailed description, reference is made to the accompanying drawings which form a p art hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses a method and system for programming neurostimulation pulse patterns using a graphical user interface (GUI). Advancements in neuroscience and neurostimulation research have led to a demand for using complex and/or individually optimized patterns of neurostimulation pulses for various types of therapies. The capability of a neurostimulation system in treating various types of disorders will be limited by the programmability of such patterns of neurostimulation pulses. Because such a task may be performed at least in part by a user such as a physician or other caregiver with the patient in a clinical setting, there is a need for an intuitive, user-friendly method and system for programming the neurostimulation pulse pattern.

The present system allows for definition of a pattern of neurostimulation pulses using a graphical method. In various embodiments, the GUI allows the pattern of neurostimulation pulses to be defined using various parameters each specified as a function a time and presented as a graphically adjustable curve. In various embodiments, defining a complex pattern of neurostimulation pulses using a few variable parameters substantially reduces the amount of user interaction required to create and adjust the pattern, for example when compared to an existing method of tedious control of various parameters for numerous pulses in the pattern. The reduced amount of user interaction may allow changes to the pattern of neurostimulation pulses to be made in real time.

In various embodiments, the present system facilitates creation and adjustment of complex patterns of neurostimulation pulses, such as a pattern that includes sequences of short bursts of pulses where the bursts and the pulses may each have different amplitude and timing parameters. In various embodiments, an envelope curve is generated from various parameter curves, such as a frequency curve, a duration (pulse width) curve, and an amplitude curve. The envelope curve also specifies on-periods (active segments) and off-periods (inactive segments). One or more neurostimulation pulses are delivered during each of the on-periods, and no neroustimulation pulses is delivered during each of the off-periods. The on-periods are each assigned to a specified pulse type, which can be graphically created and/or adjusted using the GUI. The waveform of each neurostimulation pulse in pattern (under the envelope curve) is scaled by the amplitude curve and the duration curve. Thus, each specified pulse type may be scaled into several different pulse types, thereby reducing the effort for creating individual pulses. The frequency curve controls the frequency (or inter-pulse interval) at which the pulses are to be delivered during each of the on-periods. Once the envelope curve and the specified pulse types are generated, parameters describing them may be generated and programmed into a stimulation device, such as an implantable neurostimulator (also referred to as an implantable pulse generator, or IPG). In various embodiments, the GUI also allows for definition of current steering (i.e. electrode fractionalization) for each of the specified pulse types.

In various embodiments, the present system enable fast and intuitive definition of patterns of neurostimulation pulses in a way that allows the patterns to be designed, tested, and modified in real time. While an envelope curve generated from a frequency curve, a duration (pulse width) curve, and an amplitude curve is discussed as a specific example, the present subject matter allows for definition of a pattern of neurostimulation pulses using an envelope curve generated by any one or more curves each representing a parameter that can be specified as a function of time. While the application in neurostimulation is discussed as a specific example, the present subject matter allows for waveform definition in any electrical stimulation and other medical device applications in which a waveform representing a pattern or sequence of pulses is to be defined.

FIG. 1 illustrates an embodiment of a neurostimulation system 100. System 100 includes electrodes 106, a stimulation device 104, and a programming device 102. Electrodes 106 are configured to be placed on or near one or more neural targets in a patient. Stimulation device 104 is configured to be electrically connected to electrodes 106 and deliver neurostimulation energy, such as in the form of electrical pulses, to the one or more neural targets though electrodes 106. The delivery of the neurostimulation is controlled by using a plurality of stimulation parameters, such as stimulation parameters specifying a pattern of the electrical pulses and a selection of electrodes through which each of the electrical pulses is delivered. In various embodiments, at least some parameters of the plurality of stimulation parameters are programmable by a user, such as a physician or other caregiver who treats the patient using system 100. Programming device 102 provides the user with accessibility to the user-programmable parameters. In various embodiments, programming device 102 is configured to be communicatively coupled to stimulation device via a wired or wireless link.

In various embodiments, programming device 102 includes a graphical user interface (GUI) that allows the user to set and/or adjust values of the user-programmable parameters by creating and/or editing graphical representations of various waveforms. Such waveforms may include, for example, the waveform of a pattern of neurostimulation pulses to be delivered to the patient as well as individual waveforms that are used as building blocks of the pattern of neurostimulation pulses, such as the waveform of each pulse in the pattern of neurostimulation pulses. The user may also be allowed to define an electrode selection specific to each individually defined waveform.

Figure 2:
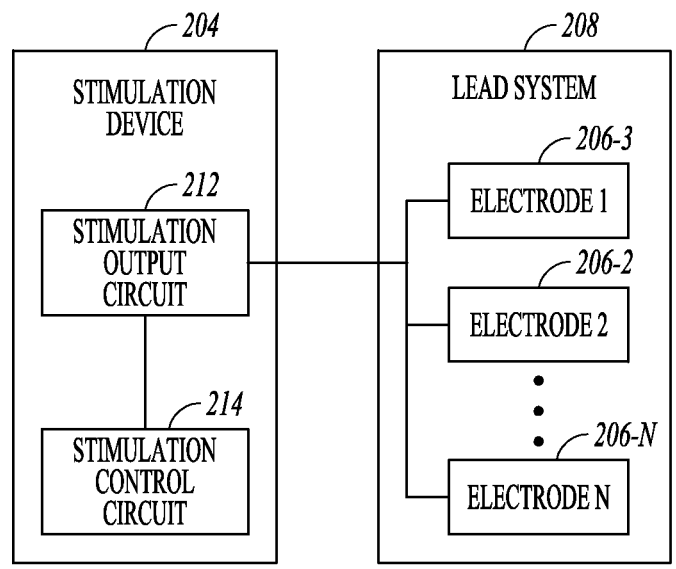
FIG. 2 illustrates an embodiment of a stimulation device and a lead system, such as may be implemented in the neurostimulation system of FIG. 1.

FIG. 2 illustrates an embodiment of a stimulation device 204 and a lead system 208, such as may be implemented in neurostimulation system 100. Stimulation device 204 represents an embodiment of stimulation device 104 and includes a stimulation output circuit 212 and a stimulation control circuit 214. Stimulation output circuit 212 produces and delivers neurostimulation pulses. Stimulation control circuit 214 controls the delivery of the neurostimulation pulses using the plurality of stimulation parameters, which specifies a pattern of the neurostimulation pulses. Lead system 208 includes one or more leads each configured to be electrically connected to stimulation device 204 and a plurality of electrodes 206 distributed in the one or more leads. The plurality of electrodes 206 includes electrode 206-1, electrode 206-2, . . . electrode 206-N, each a single electrically conductive contact providing for an electrical interface between stimulation output circuit 212 and tissue of the patient, where N≥2. The neurostimulation pulses are each delivered from stimulation output circuit 212 through a set of electrodes selected from electrodes 206. In various embodiments, the neurostimulation pulses may include one or more individually defined pulses, and the set of electrodes may be individually definable by the user for each of the individually defined pulses.

In various embodiments, the number of leads and the number of electrodes on each lead depend on, for example, the distribution of target(s) of the neurostimulation and the need for controlling the distribution of electric field at each target. In one embodiment, lead system 208 includes 2 leads each having 8 electrodes.

Figure 3:
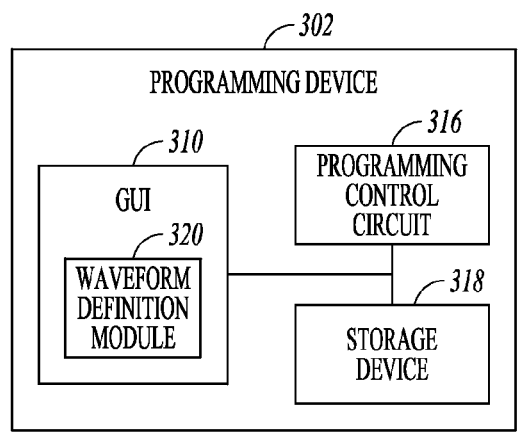
FIG. 3 illustrates an embodiment of a programming device, such as may be implemented in the neurostimulation system of FIG. 1.

FIG. 3 illustrates an embodiment of a programming device 302, such as may be implemented in neurostimulation system 100. Programming device 302 represents an embodiment of programming device 102 and includes a storage device 318, a programming control circuit 316, and a GUI 310. Storage device 318 stores a stimulation waveform representing a pattern of neurostimulation pulses during a stimulation period. Programming control circuit 316 generates the plurality of stimulation parameters that controls the delivery of the neurostimulation pulses according to the stimulation waveform. GUI 310 represents an embodiment of GUI 110 and includes a waveform definition module 320 that allows for definition of the pattern of neurostimulation pulses by creating and/or adjusting the stimulation waveform using a graphical method. In various embodiments, GUI 310 allows the user to define the stimulation waveform as a function of one or more adjustable parameter curves each being a function of time during the stimulation period. The one or more adjustable parameter curves each represent a user-programmable parameter. Waveform definition module 320 is configured to present the stimulation waveform, present each parameter curve, allow for adjustment of each parameter curve, and update the stimulation waveform in response to the adjustment of each parameter curve.

In various embodiments, GUI 310 includes any type of presentation device, such as interactive or non-interactive screens, and any type of user input devices that allow the user to edit the graphical representation of the accessed waveform, such as touchscreen, keyboard, keypad, touchpad, trackball, joystick, and mouse. In one embodiment, GUI 310 includes an interactive touchscreen and displays the graphical representation of the accessed waveform by visually indicating parameters defining the accessed waveform on the touchscreen. The touchscreen allows the user to modify one or more parameters of the visually indicated parameters, such as by dragging one or more segments of the accessed waveform.

In various embodiments, circuits of neurostimulation 100, including its various embodiments discussed in this document, may be implemented using a combination of hardware and software. For example, the circuit of GUI 110, stimulation control circuit 214, and programming control circuit 316, including their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 4:
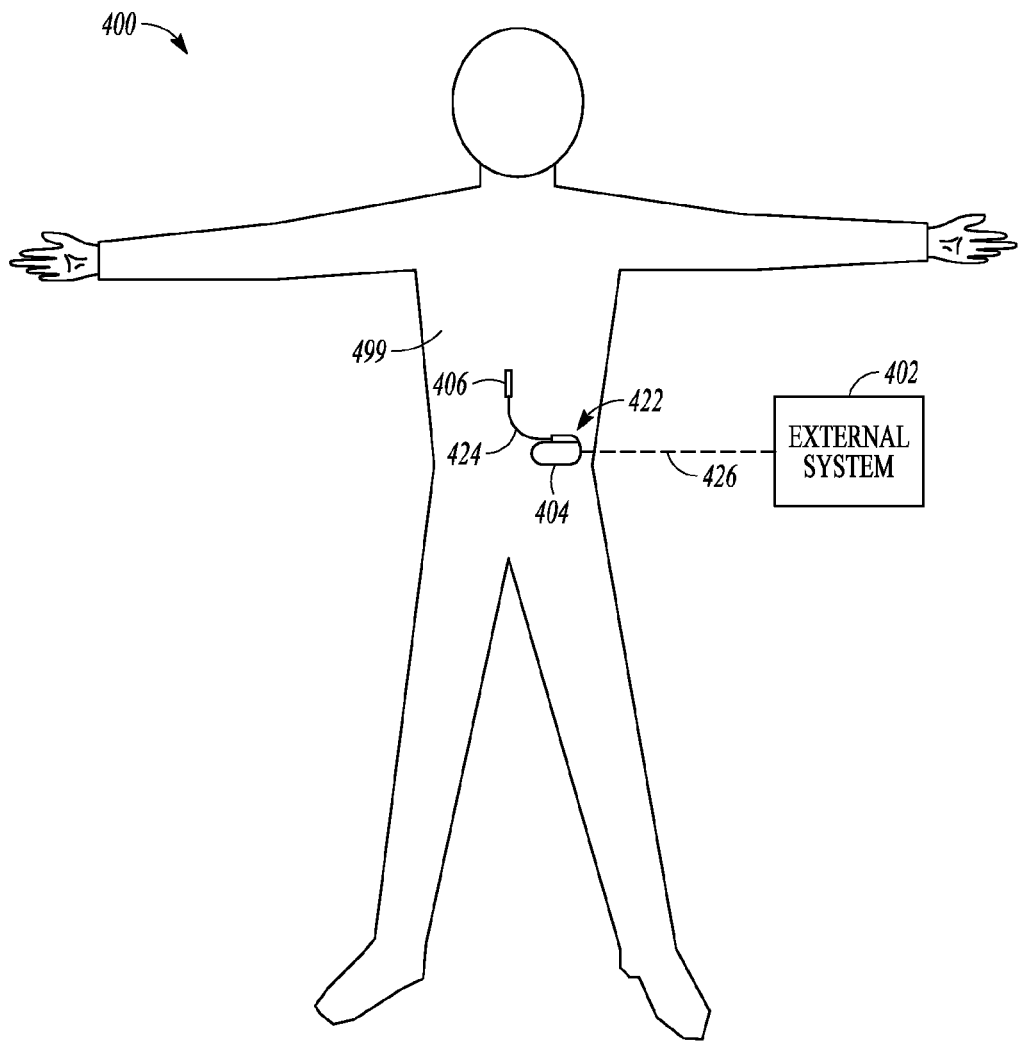
FIG. 4 illustrates an implantable neurostimulation system and portions of an environment in which the implantable neurostimulation system may be used.

FIG. 4 illustrates an implantable neurostimulation system 400 and portions of an environment in which system 400 may be used. System 400 includes an implantable system 422, an external system 402, and a telemetry link 426 providing for wireless communication between implantable system 422 and external system 402. Implantable system 422 is illustrated in FIG. 4 as being implanted in a patient's body 499.

Implantable system 422 includes an implantable stimulator (also referred to as an implantable pulse generator, or IPG) 404, a lead system 424, and electrodes 406, which represent an embodiment of stimulation device 204, lead system 208, and electrodes 206, respectively. External system 402 represents an embodiment of programming device 302. In various embodiments, external system 402 includes one or more external (non-implantable) devices each allowing the user and/or the patient to communicate with implantable system 422. In some embodiments, external 402 includes a programming device intended for the user to initialize and adjust settings for implantable stimulator 404 and a remote control device intended for use by the patient. For example, the remote control device may allow the patient to turn implantable stimulator 404 on and off and/or adjust certain patient-programmable parameters of the plurality of stimulation parameters.

Figure 5:
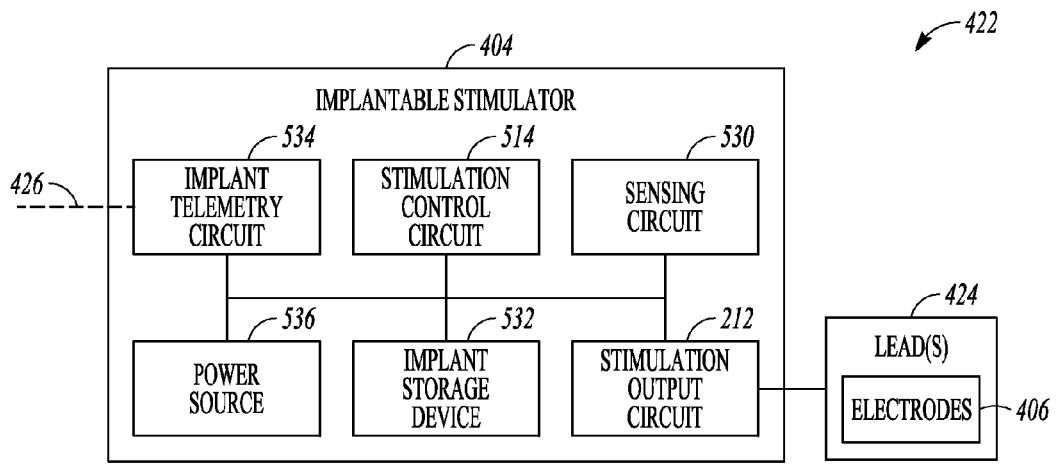
FIG. 5 illustrates an embodiment of an implantable stimulator and one or more leads of an implantable neurostimulation system, such as the implantable neuro stimulation system of FIG. 4.

FIG. 5 illustrates an embodiment of implantable stimulator 404 and one or more leads 424 of an implantable neurostimulation system, such as implantable system 422. Implantable stimulator 404 may include a sensing circuit 530 that is optional and required only when the stimulator has a sensing capability, stimulation output circuit 212, a stimulation control circuit 514, an implant storage device 532, an implant telemetry circuit 534, and a power source 536. Sensing circuit 530, when included and needed, senses one or more physiological signals for purposes of patient monitoring and/or feedback control of the neurostimulation. Examples of the one or more physiological signals include neural and other signals each indicative of a condition of the patient that is treated by the neurostimulation and/or a response of the patient to the delivery of the neurostimulation. Stimulation output circuit 212 is electrically connected to electrodes 406 through lead 424, and delivers each of the neurostimulation pulses through a set of electrodes selected from electrodes 406. Stimulation control circuit 514 represents an embodiment of stimulation control circuit 214 and controls the delivery of the neurostimulation pulses using the plurality of stimulation parameters specifying the pattern of neurostimulation pulses. In one embodiment, stimulation control circuit 514 controls the delivery of the neurostimulation pulses using the one or more sensed physiological signals. Implant telemetry circuit 534 provides implantable stimulator 404 with wireless communication with another device such as a device of external system 402, including receiving values of the plurality of stimulation parameters from external system 402. Implant storage device 532 stores values of the plurality of stimulation parameters. Power source 536 provides implantable stimulator 404 with energy for its operation. In one embodiment, power source 536 includes a battery. In one embodiment, power source 536 includes a rechargeable battery and a battery charging circuit for charging the rechargeable battery. Implant telemetry circuit 534 may also function as a power receiver that receives power transmitted from external system 402 through an inductive couple.

In various embodiments, sensing circuit 530 (if included), stimulation output circuit 212, stimulation control circuit 514, implant telemetry circuit 534, implant storage device 532, and power source 536 are encapsulated in a hermetically sealed implantable housing. In various embodiments, lead(s) 424 are implanted such that electrodes 406 are places on and/or around one or more targets to which the neurostimulation pulses are to be delivered, while implantable stimulator 404 is subcutaneously implanted and connected to lead(s) 424 at the time of implantation.

Figure 6:
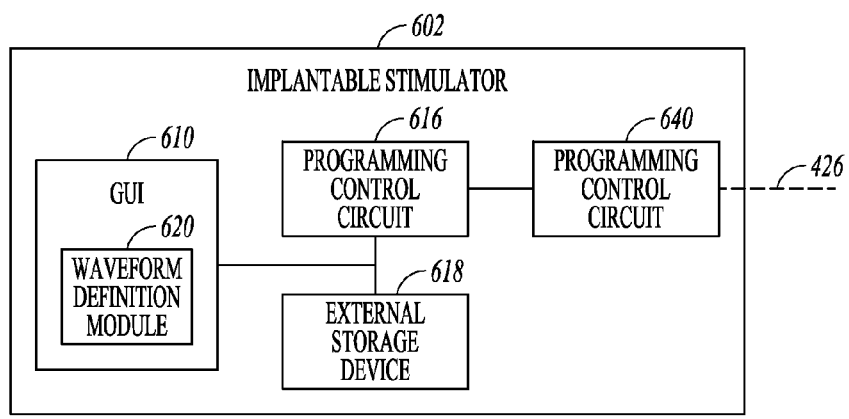
FIG. 6 illustrates an embodiment of an external programmer of an implantable neurostimulation system, such as the implantable neurostimulation system of FIG. 4

FIG. 6 illustrates an embodiment of an external programmer 602 of an implantable neurostimulation system, such as external system 402 of system 400. External programmer 602 represents an embodiment of programming device 302, and includes an external telemetry circuit 640, an external storage device 618, a programming control circuit 616, and a GUI 610.

External telemetry circuit 640 provides external programmer 602 with wireless communication with another device such as implantable stimulator 404 via telemetry link 426, including transmitting the plurality of stimulation parameters to implantable stimulator 404. In one embodiment, external telemetry circuit 640 also transmits power to implantable stimulator 404 through an inductive couple.

External storage device 618 stores one or more stimulation waveforms, each stimulation waveform representing a pattern of neurostimulation pulses during a stimulation period. In various embodiments, each stimulation waveform can be selected for modification by the user and/or for use in programming a stimulation device such as implantable stimulator 404 to deliver a therapy. In this document, "the stimulation waveform" includes a stimulation waveform representing a pattern of neurostimulation pulses during a stimulation period, and may include a stimulation waveform selected from external storage device 618 or a new stimulation waveform to be added to the one or more stimulation waveforms stored in external storage device 618.

In various embodiments, the stimulation waveform is definable on a pulse-by-pulse basis, and external storage device 618 includes a pulse library that stores one or more individually definable pulse waveforms each defining a pulse type of one or more pulse types. External storage device 618 also stores one or more individually definable fields. Each pulse type of the one or more pulse types is associated with a field of the one or more individually definable fields. Each field of the one or more individually definable fields is defined by one or more electrodes of the plurality of electrodes through which a pulse of the neurostimulation pulses is delivered and a current distribution of the pulse over the one or more electrodes.

Programming control circuit 616 represents an embodiment of programming control circuit 316 and generates the plurality of stimulation parameters, which is to be transmitted to implantable stimulator 404, based on the pattern of neurostimulation pulses. The pattern may be created and/or adjusted by the user using GUI 610 and stored in external storage device 618. In various embodiments, programming control circuit 616 checks values of the plurality of stimulation parameters against safety rules to limit these values within constraints of the safety rules. In one embodiment, the safety rules are heuristic rules.

GUI 610 represents an embodiment of GUI 310 and allows the user to define the pattern of neurostimulation pulses by creating and/or editing the stimulation waveform representing the pattern. GUI 610 defines the stimulation waveform as a function of one or more adjustable parameter curves each being a function of time during the stimulation period. The one or more adjustable parameter curves each representing a user-programmable parameter. Examples of the one or more adjustable parameter curves include a frequency curve representing a pulse frequency, a duration curve representing a pulse width, and an amplitude curve representing a pulse amplitude.

GUI 610 includes a waveform definition module 620, which represents an embodiment of waveform definition module 320. Waveform definition module 620 presents the stimulation waveform, presents each parameter curve of the one or more adjustable parameter curves, allows the user to adjust each parameter curve, and updates the stimulation waveform in response to the adjustment of each parameter curve. In one embodiment, waveform definition module 620 presents the stimulation waveform in the form of an envelope curve with one or more indicators of one or more pulse types. The envelope curve specifies on-periods (active segments) each including one or more neurostimulation pulses and off-periods (inactive segments) including no neurostimulation pulse. The on-periods are each labelled or otherwise associated with a specified pulse type, which can be graphically created and/or adjusted using the GUI. The waveform of each neurostimulation pulse in the stimulation waveform is scaled by the amplitude curve and the duration curve. In one embodiment, waveform definition module 620 presents one or more handles each placed on a parameter curve of the one or more adjustable parameter curves. The one or more handles each correspond to a value of the user-programmable parameter represented by the parameter curve. Waveform definition module 620 allows the user to adjust the parameter curve by moving each of the one or more handles on the parameter curve. In one embodiment, waveform definition module 620 allows the user to place a new handle on the parameter curve and delete a handle from the one or more handles that are already p laced on the parameter curve.

In one embodiment, waveform definition module 620 provides the user with a template waveform that can be used to create a new stimulation waveform. The template waveform is a predefined stimulation waveform representing a predefined pattern of neurostimulation pulses. External storage device 618 can include a pattern library including one or more template waveforms. Waveform definition module 620 allows the user to select a template waveform from the template library and present the selected template waveform as the stimulation waveform. In one embodiment, waveform definition module 620 allows the user to create template waveforms. For example, waveform definition module 620 may allow the user to adjust a template waveform and add the adjusted template waveform as a new template waveform to the one or more template waveforms of the pattern library.

In one embodiment, waveform definition module 620 allows the user to select of one or more on-periods in envelope curve of the stimulation waveform and assign the selected one or more on-periods to a specified pulse type stored in external storage device 618. In one embodiment, waveform definition module 620 allows the user to create a new pulse type to be added to the pulse library in external storage device 618. In one embodiment, waveform definition module 620 allows the user to select and adjust each pulse type of the one or more pulse types in the pulse library. In one embodiment, waveform definition module 620 presents a pulse waveform of a pulse type selected from the one or more pulse types and allows the user to modify the pulse waveform of the selected pulse type. In one embodiment, waveform definition module 620 presents one or more handles each placed on the pulse waveform of the selected pulse type, allows the user to select a handle from the one or more handles placed on the pulse waveform of the selected pulse type, and allows the user to modify the pulse waveform of the selected pulse type by moving the selected handle. In other words, the pulse waveform may be graphically adjusted in a way similar to the adjustment of a parameter curve of the one or more adjustable parameter curves.

In various embodiments, GUI 610 allows for export of a stimulation waveform of the one or more stimulation waveforms stored in external storage device 618 from external programmer 602. In various embodiments, GUI 610 allows for import of a stimulation waveform into external programmer 602 to be added to the one or more stimulation waveforms stored in external storage device 618. In various embodiments, GUI 610 allows for export of one or more pulse types and/or fields stored in external storage device 618 from external programmer 602. In various embodiments, GUI 610 allows for import of one or more pulse types and/or fields into external programmer 602 to be added to the one or more pulse types and/or fields stored in external storage device 618. Such imports and exports enable the user to share stimulation waveforms and/or their building blocks with other users in a community of users that use the same or similar neurostimulation systems to treat patients.

Figure 7:
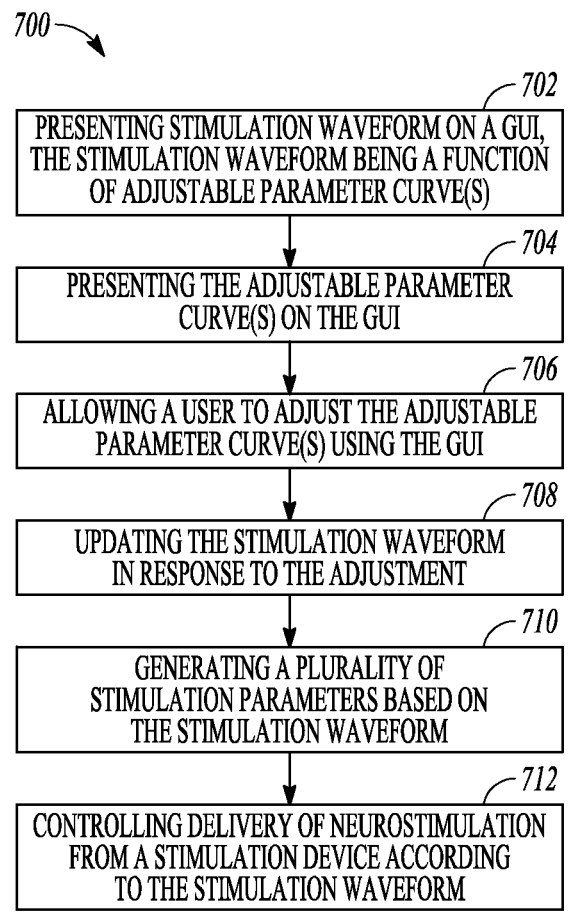
FIG. 7 illustrates an embodiment of a method for defining a stimulation waveform.
Figure 8:
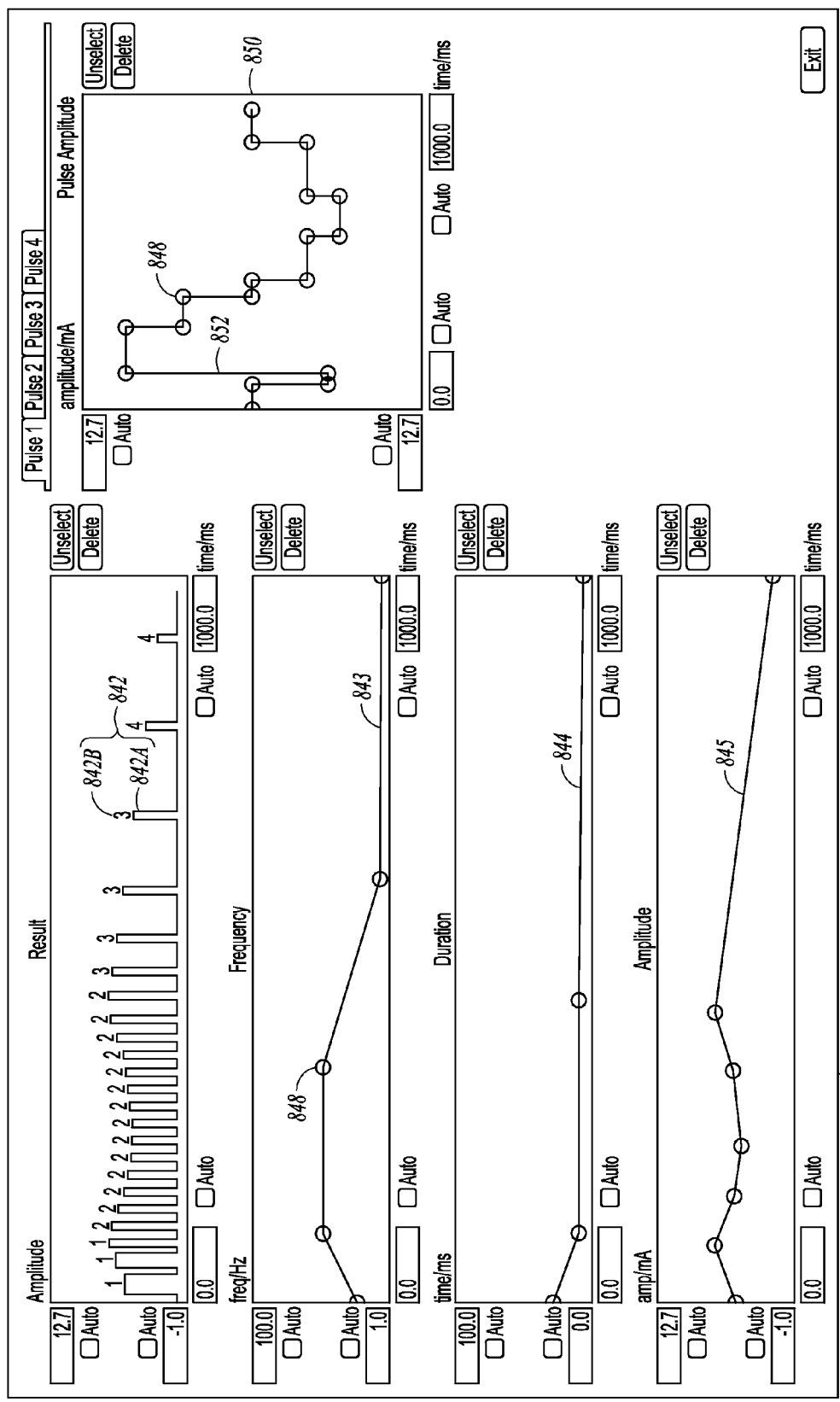
FIG. 8 illustrates an embodiment of a screen of a graphical user interface (GUI) displaying the stimulation waveform.
Figure 9:
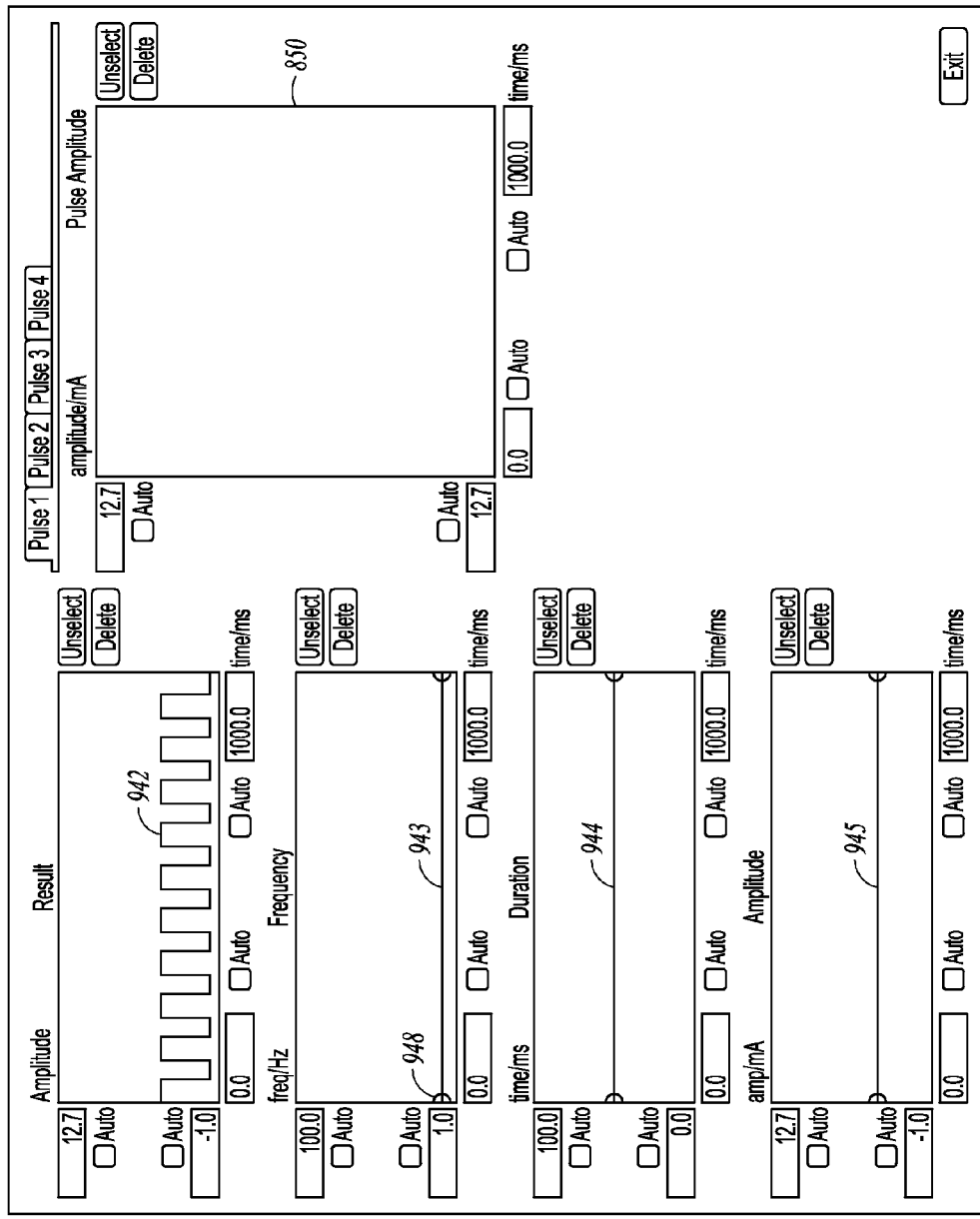
FIG. 9 illustrates an embodiment of the screen of the GUI displaying a template for the stimulation waveform.
Figure 10:
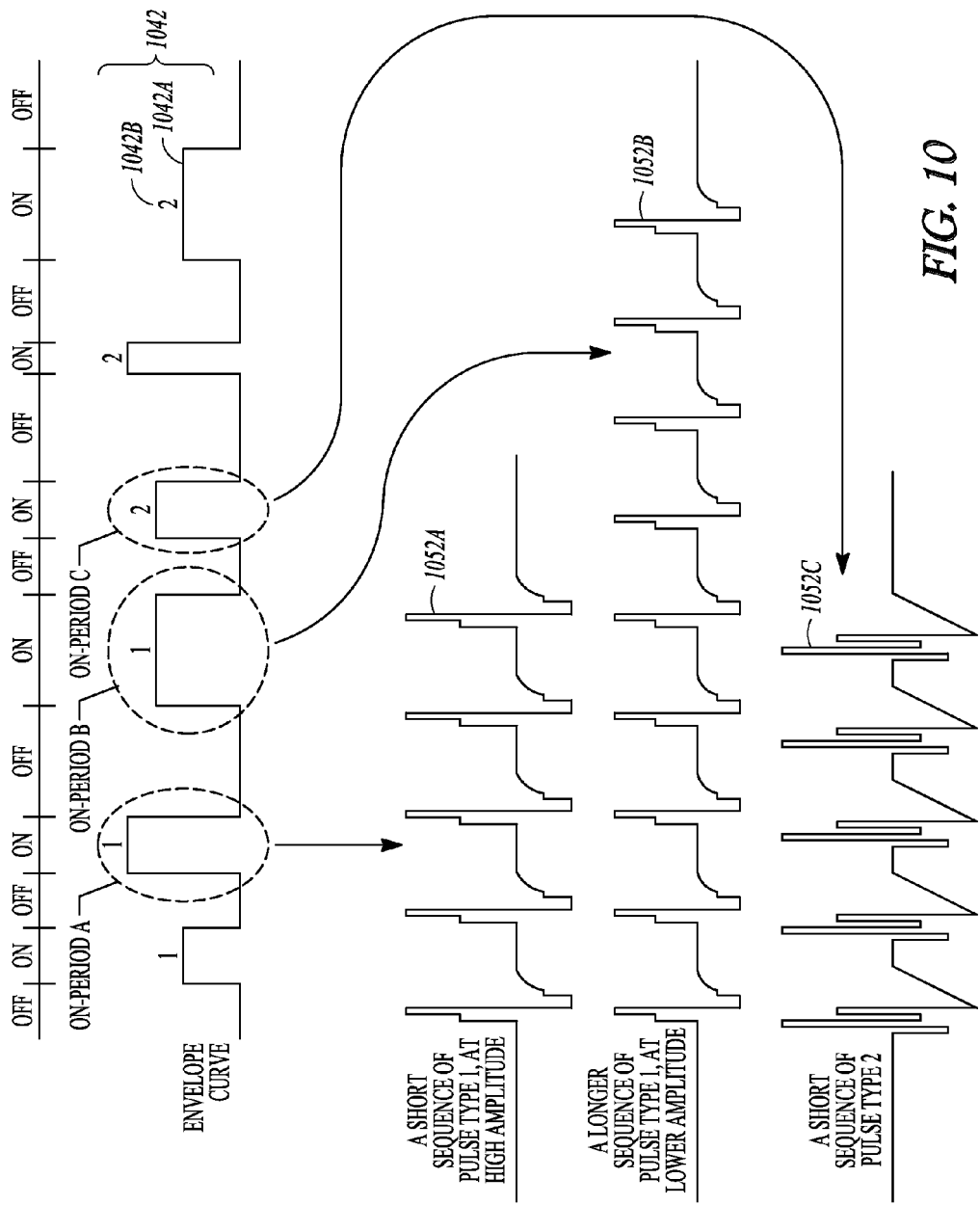
FIG. 10 illustrates an embodiment of the stimulation waveform including an envelope curve and neurostimulation pulses

FIG. 7 illustrates an embodiment of a method 700 for defining a stimulation waveform representing a pattern of neurostimulation pulses. In one embodiment, method 700 is performed using system 100, including its various embodiments as discussed in this document. In one embodiment, GUI 110, 310, or 610 is configured for performing method 700. FIG. 8 illustrates an embodiment of a screen 840 of a GUI, such as GUI 110, 310, or 610, for displaying the stimulation waveform, among other things, when method 700 is performed. FIG. 9 illustrates an embodiment of screen 840 displaying a template for the stimulation waveform. FIG. 10 illustrates an embodiment of the stimulation waveform showing a portion of the waveform including an envelope curve and neurostimulation pulses.

At 702, the stimulation waveform to be defined is presented on a GUI, such as GUI 110, 310, or 610. An example of the stimulation waveform is shown in FIG. 8 as a stimulation waveform 842. The stimulation waveform is adjustable by a user, such as a physician or other caregiver, using the GUI. The stimulation waveform represents the pattern of neurostimulation pulses during a stimulation period. In various embodiments, the stimulation waveform is defined by an envelope curve. The envelope curve specifies on periods during which the neurostimulation are delivered and off-periods during with none of the neurostimulation pulses is delivered, and is defined by one or more parameter curves representing parameters that can each be expressed as a function of time during the stimulation period. In various embodiments, the one or more parameter curves include one or more adjustable parameter curves representing one or more user-programmable parameters each being a function of time during the stimulation period.

In other words, the stimulation waveform is a function of at least the one or more adjustable parameter curves.

In various embodiments, the stimulation waveform is presented on the GUI as the envelope curve with indicator of pulse type for each of the on-periods. For example, as illustrated in FIG. 8, stimulation waveform 842 includes an envelope curve 842A and pulse type labels 842B. Pulse type labels 842B are the indicators of pulse type and each specify a pulse type to which the neurostimulation pulses in one of the on-periods are assigned to. In the illustrated example, pulse type labels 842B are each a number, with "1" indicating pulse type 1 ("Pulse 1" as displayed on screen 840), "2" indicating pulse type 2 ("Pulse 2" as displayed on screen 840), and so on.

In one embodiment, a template waveform is presented as the stimulation waveform at a beginning of a process of defining the stimulation waveform. In one embodiment, the user is allowed to select the template waveform from one or more template waveforms stored in a storage device. A template waveform is a predefined stimulation waveform representing a predefined pattern of neurostimulation pulses. An example of the template waveform is shown in FIG. 9 as a stimulation waveform 942. The storage device may include a pattern library including one or more basic template waveforms and/or one or more therapy-specific template waveforms. A basic template waveform serves as a beginning point, for example, for the user to create a new custom stimulation waveform. A therapy-specific template waveform serves as a default waveform, for example, for a specific type of neurostimulation therapy that may be used to treat a patient with or without modification as determined by the user.

At 704, the one or more adjustable parameter curves are presented on the GUI. The presented one or more adjustable parameter curves correspond to the presented stimulation waveform. In one embodiment, as illustrated in FIG. 8, the one or more adjustable parameter curves may include a frequency curve 843 representing a pulse frequency for the stimulation waveform, a duration curve 844 representing a pulse width for the stimulation waveform, and an amplitude curve 845 representing a pulse amplitude for the stimulation waveform. Thus, stimulation waveform 842 is a function of frequency curve 843, duration curve 844, and amplitude curve 845. Stimulation waveform 942, which is illustrated in FIG. 9, is the template waveform. A template frequency curve 943, a template duration curve 944, and a template amplitude curve 945 are presented as the adjustable parameter curves correspond to stimulation waveform 942. Shown in FIG. 9 by way of example, stimulation waveform 942 represents a template waveform for a stimulation periods of 1000 ms. Template frequency curve 943 as shown in FIG. 9 represents a pulse frequency of 10 Hz over the stimulation period. Template duration curve 943 as shown in FIG. 9 represents a pulse width of 50 ms over the stimulation period. Template amplitude curve 943 as shown in FIG. 9 represents a pulse amplitude of 4 mA over the stimulation period. In various embodiments, the one or more parameter curves may include any one or any combination of frequency curve 843, duration curve 844, amplitude curve 845, and one or more other parameters that should each be represented as a function of time during the stimulation period.

In various embodiments, the stimulation waveform as presented on the GUI indicates at least the envelope curve and the indicators of pulse type for each of the on-periods of the envelope curve. In various embodiments, the envelope curve as presented on the GUI shows at least the on-periods and the off-periods. In one envelopment, the envelope curve may have an amplitude corresponding to the amplitude of the neurostimulation pulses. For example, as illustrated in FIG. 8, envelope curve 842A has an amplitude corresponding to amplitude curve 845. In other embodiments, the envelope curve may have an amplitude corresponding any of the one or more adjustable parameter curves or a function of any one of the one or more adjustable parameter curves or any combination of adjustable parameter curves. For example, the envelope curve may have an amplitude corresponding to the pulse amplitude for the stimulation waveform, the pulse amplitude for the stimulation waveform, the pulse frequency for the stimulation waveform, or an energy or intensity of the stimulation waveform that is a function of the pulse amplitude, the pulse width, and/or the pulse frequency of the stimulation waveform.

At 706, the user is allowed to adjust the one or more adjustable parameter curves using the GUI. The user is allowed to model each user-programmable parameter of the one or more user-programmable parameters for the stimulation period by adjusting the parameter curve representing that user-programmable parameter. In various embodiments, one or more handles are each placed on a curve of the one or more adjustable parameter curves. The one or more handles each correspond to a value of the programmable parameter represented by the curve. In the embodiment illustrated in FIG. 8, circular handles 848 are placed in each of frequency curve 843, duration curve 844, and amplitude curve 845. In the embodiment illustrated in FIG. 9, default handles 948 are placed at both ends of template frequency curve 943, template duration curve 944, and template amplitude curve 945 when the template stimulation waveform 942 is displayed (before adjustment by the user). In various embodiments, the user is allowed to place one or more additional handles to the one or more handles placed on the curve. For example, the user may be allowed to place an additional handle by right-clicking a mouse or touchpad of the GUI. In various embodiments, the user is allowed to select each handle of the one or more handles on the each curve. For example, the user may be allowed to select the handle by left-clicking the mouse or touchpad of the GUI. The user can then move the selected handle along the each curve. The user is also allowed to deselect the selected handle and, when needed, select a different handle. In various embodiments, the user may be allowed to delete one or more handles from the one or more handles p laced on the curve.

At 708, the stimulation waveform is updated in response to the adjustment to the one or more adjustable parameter curves made by the user. For example, stimulation waveform 842 is updated in response to the adjustment made to frequency curve 843, duration curve 844, and amplitude curve 845. The stimulation waveform is updated to reflect each change made to a programmable parameter of the one or more programmable parameters. In one embodiment, the stimulation waveform is updated automatically up on the each change made by the user. In another embodiment, the stimulation waveform is updated in response to an update command entered by the user.

In various embodiments, each on-period in the envelope curve may be assigned to a pulse type specified by the user. The user may be allowed to select one or more on-periods (each including one or more neurostimulation pulses) in the envelope curve and assign the selected one or more on-periods to the specified pulse type. One or more pulse types each including a pulse waveform may be stored and available for selection by the user. For example, as illustrated in FIG. 8, envelope curve 842A includes on-periods each being assigned to one of pulse types 1-4. When an on-period is assigned to the specified pulse type, the pulse waveform for that neurostimulation pulse is scaled according to the envelope curve. In various embodiments, the user is allowed to define each pulse type of the stored one or more pulse types. This may include modifying any one of the stored one or more pulse types and/or creating a new pulse type to be added to the stored one or more pulse types. The new pulse type may be created by modifying one of the stored one or more pulse types and adding the modified pulse type as a new pulse type to the stored one or more pulse types.

In one embodiment, as illustrated in FIG. 8, a pulse builder 850 is presented on the screen of the GUI to allow for modification of each of the stored one or more pulse types (illustrated as Pulses 1-4) and addition of new pulse types. As shown in FIG. 8 as an example, in response to the pulse type "Pulse 1" being selected, a pulse waveform 852 is presented in pulse builder 850, with handles 848 each placed on pulse waveform 852, such as at each turning point of pulse waveform 852 (as shown). In various embodiments, the user is allowed to place one or more additional handles on pulse waveform 852. For example, the user may be allowed to place an additional handle by right-clicking a mouse or touchpad of the GUI. In various embodiments, the user is allowed to select each handle of the one or more handles on the each curve. For example, the user may be allowed to select the handle by left-clicking the mouse or touchpad of the GUI. The user can then move the selected handle along pulse waveform 852. The user is also allowed to deselect the selected handle and, when needed, select a different handle. In various embodiments, the user may be allowed to delete one or more handles from the one or more handles placed on pulse waveform 852.

In one embodiment, a pulse library including one or more template pulse types is stored. The user may customize each pulse type used in the stimulation waveform by selecting a template pulse type from the pulse library and modifying the pulse waveform of the selected template pulse type. The customized pulse type may also be added to the pulse library, for example as a therapy-specific and/or patient-specific template pulse type that includes special features in the pulse waveform.

FIG. 10 illustrates an embodiment of a portion of a stimulation waveform 1042 including an envelope curve 1042A and pulse type labels 1042B, as a specific example of stimulation waveform 842 including envelope curve 842A and pulse type labels 842B. Envelope curve 1042A includes on-periods ("ON") and off-periods ("OFF"). Each of the on-periods includes one or more neurostimulation pulses. For the purpose of illustration, FIG. 10 shows neurostimulation pulses of three of the on-periods, "ON-PERIOD A", "ON-PERIOD B", and "ON-PERIOD C", each of which includes a burst of neurostimulation pulses. The neurostimulation pulses of ON-PERIOD A each have a pulse waveform 1052A. The neurostimulation pulses of ON-PERIOD B each have a pulse waveform 1052B. The neurostimulation pulses of ON-PERIOD C each have a pulse waveform 1052C. Envelope curve 1042A indicates the on-periods and the off-periods and the amplitude of the stimulation waveform. ON-PERIOD A and ON-PERIOD B are assigned to the same pulse type 1, but ON-PERIOD B is longer than ON-PERIOD A, and the amplitude of the neurostimulation pulses of ON-PERIOD B is lower than the amplitude of the neurostimulation pulses of ON-PERIOD A. In other words, pulse waveforms 1052A and 1052B have the same shape but scaled to different amplitudes by envelope curve 1042A. ON-PERIOD A and ON-PERIOD C are similar or equal in length, but assigned to different pulse types (1 and 2, respectively), and the amplitude of the neurostimulation pulses of ON-PERIOD C is lower than the amplitude of the neurostimulation pulses of ON-PERIOD A. In other words, pulse waveforms 1052A and 1052C have different shapes and scaled to different amplitudes by envelope curve 1042A. ON-PERIOD B and ON-PERIOD C are assigned to different pulse types (1 and 2, respectively), and ON-PERIOD C is shorter than ON-PERIOD B, but the amplitude of the neurostimulation pulses of ON-PERIOD B is similar or equal to the amplitude of the neurostimulation pulses of ON-PERIOD A. In other words, pulse waveforms 1052B and 1052C have different shapes but scaled to similar to identical amplitudes by envelope curve 1042A.

At 710, a plurality of stimulation parameters is generated based on the stimulation waveform. In other words, the stimulation waveform is converted into a plurality of stimulation parameters. In one embodiment, the plurality of stimulation parameters is generated in response to a command entered by the user upon completing a process of defining the stimulation waveform. The plurality of stimulation parameters is transmitted to a stimulation device, such as stimulation device 104 or 204. In one embodiment, the plurality of stimulation parameters is transmitted to an implantable stimulator from an external programmer via telemetry, such as being transmitted to implantable stimulator 404 from external programmer 602 via telemetry link 426.

At 712, delivery of neurostimulation pulses from the stimulation device is controlled according to the stimulation waveform, by using the plurality of stimulation parameters. Examples of the stimulation device includes stimulation device 104 or 204. In one embodiment, the neurostimulation pulses are delivered from an implantable stimulator, such as implantable stimulator 404, and the delivery is controlled using the plurality of stimulation parameters transmitted to the implantable stimulator.

In various embodiments, the present system may be combined into a programming device that applies one or more other methods for defining patterns of neurostimulation pulses. Method 700 may be performed using a programming device that is also configured to perform one or more other graphical and/or non-graphical methods for defining patterns of neurostimulation pulses. An example of another graphical method for programming the pattern of neurostimulation pulses is discussed in U.S. Provisional Patent Application Ser. No. 62/050,505, entitled "GRAPHICAL USER INTERFACE FOR PROGRAMMING NEURO STIMULATION PULSE PATTERNS," filed on Sep. 15, 2014, assigned to Boston Scientific Neuromodulation Corporation, which is incorporated by reference in its entirety. In various embodiments, the user may define the pattern of neurostimulation pulses by using building blocks, such as waveforms and electrode assignments, created by using various methods. For example, when assigning pulses in the stimulation waveform to specified pulse types during a performance of method 700, the user may specify one or more pulse types, including the pulse waveform and its field (electrode selection and current distribution), that are created using another method (such as the method discussed in U.S. Provisional Patent Application Ser. No. 62/050,505) and stored in the pulse library.

It is to be understood that the above detailed description is intended to be illustrative, and not restrictive. Other embodiments will be apparent to those of skill in the art up on reading and understanding the above description. The

What is claimed is:

1. A neurostimulation system configured to allow for control of neurostimulation by a user, comprising:
 a storage device configured to store a stimulation waveform representing a pattern of neurostimulation pulses during a stimulation period;
 a programming control circuit configured to generate a plurality of stimulation parameters controlling delivery of the neurostimulation pulses according to the stimulation waveform; and
 a graphical user interface (GUI) coupled to the storage device and the control circuit and configured to define the stimulation waveform as a function of one or more adjustable parameter curves each being a function of time during the stimulation period, the one or more adjustable parameter curves each representing a user-programmable parameter, the GUI including a waveform definition module configured to:
 present the stimulation waveform;
 present each parameter curve of the one or more adjustable parameter curves as a graphically adjustable curve;
 allow for adjustment of the each parameter curve using a graphical method performed by the user; and
 update the stimulation waveform in response to the adjustment of the each parameter curve.

2. The system of claim 1, further comprising a stimulation device including:
 a stimulation output circuit configured to deliver the neurostimulation pulses; and
 a stimulation control circuit configured to control the delivery of the neurostimulation pulses using the plurality of stimulation parameters; and
 a programming device communicatively coupled to the stimulation device and including the storage device, the programming circuit, and the GUI.

3. The system of claim 2, wherein the stimulation device comprises an implantable stimulator including an implant telemetry circuit configured to receive the plurality of stimulation parameters, and the programming device comprises an external programmer including an external telemetry circuit configured to transmit the plurality of stimulation parameters to the implantable stimulator via a wireless telemetry link.

4. The system of claim 1, wherein the waveform definition module is further configured to:
 present one or more handles each placed on a parameter curve of the one or more adjustable parameter curves, the one or more handles each corresponding to a value of the user-programmable parameter represented by the parameter curve; and
 allow for adjustment of the parameter curve by moving a handle of the one or more handles.

5. The system of claim 4, wherein the waveform definition module is further configured to allow for addition of a new handle to the one or more handles placed on the parameter curve and deletion of a handle from the one or more handles placed on the parameter curve.

6. The system of claim 5, wherein the storage device is further configured to store a pattern library including one or more template waveforms, and the waveform definition module is further configured to select a template waveform from the template library and present the selected template waveform as the stimulation waveform.

7. The system of claim 1, wherein waveform definition module is configured to present the stimulation waveform as an envelope curve with pulse type indicators, the envelope curve specifying on-periods each including one or more pulses of the neurostimulation pulses and off-periods including none of the neurostimulation pulses, the on-periods each assigned to a pulse type of the one of more pulse types, the pulse type indicators each specifying the pulse type to which one of the on-periods is assigned to.

8. The system of claim 7, wherein the storage device is further configured to store a pulse library including one or more pulse types, and the waveform definition module is further configured to allow for selection of one or more on-periods of the on-periods in the envelope curve and assignment of the selected one or more on-periods to the specified pulse type.

9. The system of claim 8, wherein the waveform definition module is further configured to allow for creation of a new pulse type to be added to the pulse library and adjustment of each pulse type of the one or more pulse types in the pulse library.

10. A method for controlling neurostimulation by a user, comprising:
 presenting a stimulation waveform on a graphical user interface (GUI), the stimulation waveform representing a pattern of neurostimulation pulses during a stimulation period and being a function of one or more adjustable parameter curves each being a function of time during the stimulation period, the one or more adjustable parameter curves each representing a user-programmable parameter;
 presenting the one or more adjustable parameter curves each as a graphically adjustable curve on the GUI;
 allowing the user to graphically adjust each parameter curve of the one or more adjustable parameter curves using the GUI;
 updating the stimulation waveform in response to the adjustment of the each parameter curve; and
 generating a plurality of stimulation parameters based on the stimulation waveform, the plurality of stimulation parameters allowing for delivery of the neurostimulation from a stimulation device to be controlled according to the stimulation waveform.

11. The method of claim 10, wherein presenting the stimulation waveform comprises presenting a template waveform, and further comprising:
 creating one or more template waveforms;
 storing the one or more template waveforms; and
 selecting the template waveform from the stored one or more waveforms.

12. The method of claim 11, wherein creating the one or more template waveforms comprises creating one or more therapy-specific template waveforms for one or more types of neurostimulation therapy.

13. The method of claim 11, further comprising:
 presenting one or more handles on the GUI, the one or more handles each placed on a parameter curve of the one or more adjustable parameter curves, the one or more handles each corresponding to a value of the user-programmable parameter represented by the parameter curve;
 allowing the user to select a handle of the one or more handles placed on the parameter curve; and
 allowing the user to adjust the parameter curve by moving the selected handle.

14. The method of claim 13, further comprising:
allowing the user to add a new handle to the one or more handles placed on the parameter curve; and
allowing the user to delete a handle of the one or more handles placed on the parameter curve.

15. The method of claim 13, wherein presenting the one or more adjustable parameter curves comprises presenting one or more of a frequency curve representing a pulse frequency, a duration curve representing a pulse width, and an amplitude curve representing a pulse amplitude.

16. The method of claim 10, wherein presenting the stimulation waveform comprises presenting an envelope curve with pulse type indicators, the envelope curve specifying on-periods each including one or more pulses of the neurostimulation pulses and off-periods including none of the neurostimulation pulses, the on-periods each assigned to a pulse type of the one of more pulse types, the pulse type indicators each specifying the pulse type to which one of the on-periods is assigned to.

17. The method of claim 16, further comprising:
storing the one or more pulse types;
allowing the user to select one or more on-periods of the on-periods in the envelope curve;
allowing the user to select a pulse type from the stored one or more pulse types; and
allowing the user to assign the selected one or more on-periods to the selected pulse type.

18. The method of claim 17, further comprising:
allowing the user to create a new pulse type using the GUI to add to the stored one or more pulse types; and
allowing the user to modify each pulse type of the one or more pulse types using the GUI.

19. The method of claim 18, wherein allowing the user to modify the each pulse type comprises:
presenting a pulse waveform of the each pulse type on the GUI;
presenting one or more handles each placed on the pulse waveform of the each pulse type;
allowing the user to select a handle from the one or more handles placed on the pulse waveform; and
allowing the user to modify the pulse waveform by moving the selected handle.

20. The method of claim 10, further comprising:
transmitting the plurality of stimulation parameters to an implantable stimulator; and
controlling delivery of the neurostimulation pulses from the implantable stimulator using the plurality of stimulation parameters.

* * * * *